(12) United States Patent
Hadida Ruah et al.

(10) Patent No.: US 8,012,999 B2
(45) Date of Patent: Sep. 6, 2011

(54) MODULATORS OF CFTR

(75) Inventors: Sara S. Hadida Ruah, La Jolla, CA (US); Peter D. J. Grootenhuis, San Diego, CA (US); Jinglan Zhou, San Diego, CA (US); Brian Richard Bear, Oceanside, CA (US); Mark T. Miller, San Diego, CA (US); Jason McCartney, Cardiff by the Sea, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/782,967

(22) Filed: May 19, 2010

(65) Prior Publication Data
US 2010/0227888 A1   Sep. 9, 2010

Related U.S. Application Data

(63) Continuation of application No. 12/117,948, filed on May 9, 2008, now Pat. No. 7,754,739, which is a continuation-in-part of application No. 11/804,726, filed on May 18, 2007, now Pat. No. 7,659,268, which is a continuation-in-part of application No. 11/594,431, filed on Nov. 8, 2006, now Pat. No. 7,741,321.

(60) Provisional application No. 60/928,289, filed on May 9, 2007.

(51) Int. Cl.
*A61K 31/443* (2006.01)
*A61K 31/4418* (2006.01)
(52) U.S. Cl. ........................................ 514/337; 514/352
(58) Field of Classification Search .................. 514/337, 514/352
See application file for complete search history.

(56) References Cited

FOREIGN PATENT DOCUMENTS
WO   WO 2005/075435 A1 *   8/2005
* cited by examiner

*Primary Examiner* — Kamal Saeed
*Assistant Examiner* — Kristin Bianchi
(74) *Attorney, Agent, or Firm* — Michael J. DiVerdi

(57) ABSTRACT

Compounds of the present invention, and pharmaceutically acceptable compositions thereof, are useful as modulators of ATP-Binding Cassette ("ABC") transporters or fragments thereof, including Cystic Fibrosis Transmembrane Conductance Regulator ("CFTR"). The present invention also relates to methods of treating ABC transporter mediated diseases using compounds of the present invention.

20 Claims, No Drawings

MODULATORS OF CFTR

CROSS REFERENCE TO RELATED APPLICATIONS

This application is a continuing application and claims the benefit of priority under 35 USC §120 to U.S. patent application Ser. No. 12/117,948, filed May 9, 2008, which claims priority to U.S. patent application Ser. No. 11/804,726, filed May 18, 2007, which in turn claims priority to U.S. patent application Ser. No. 11/594,431, filed Nov. 8, 2006; and under 35 U.S.C. §119 to U.S. provisional patent application Ser. No. 60/928,289, filed May 9, 2007, the entire contents of each of the above applications is incorporated herein by reference.

TECHNICAL FIELD OF THE INVENTION

The present invention relates to modulators of Cystic Fibrosis Transmembrane Conductance Regulator ("CFTR"), compositions thereof, and methods therewith. The present invention also relates to methods of treating CFTR mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multi-drug resistance proteins (like the MDR1-P glycoprotein, or the multi-drug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl− channels expressed on the basolateral surface of the cell. Secondary active transport of chloride from the luminal side leads to the accumulation of intracellular chloride, which can then passively leave the cell via Cl− channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymyositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are Cystic fibrosis (due to misfolded ΔF508-CFTR as discussed above), Hereditary emphysema (due to a1-antitrypsin; non Piz variants), Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses (due to Lysosomal processing enzymes), Sandhof/Tay-Sachs (due to β-Hexosaminidase), Crigler-Najjar type II (due to UDP-glucuronyl-sialyc-transferase), Polyendocrinopathy/Hyperinsulemia, Diabetes mellitus (due to Insulin receptor), Laron dwarfism (due to Growth hormone receptor), Myleoperoxidase deficiency, Primary hypoparathyroidism (due to Preproparathyroid hormone), Melanoma (due to Tyrosinase). The diseases associated with the latter class of ER malfunction are Glycanosis CDG type 1, Hereditary emphysema (due to α1-Antitrypsin (PiZ variant), Congenital hyperthyroidism, Osteogenesis imperfecta (due to Type I, II, IV procollagen), Hereditary hypofibrinogenemia (due to Fibrinogen), ACT deficiency (due to α1-Antichymotrypsin), Diabetes insipidus (DI), Neurophyseal DI (due to Vasopvessin hormone/V2-receptor), Neprogenic DI (due to Aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs, and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrhea causing bacteria is enterotoxigenic E-coli (ETEC) having the K99 pilus antigen. Common viral causes of diarrhea include rotavirus and coronavirus. Other infectious agents include cryptosporidium, *giardia lamblia*, and *salmonella*, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of CFTR. These compounds have the general formula (I):

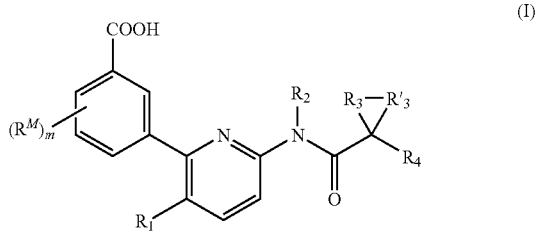

or a pharmaceutically acceptable salt thereof, wherein $R_1$, $R_2$, $R_3$, $R'_3$, $R_4$, $R^M$, m and n are described herein.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes Mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes Insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjogren's disease.

DETAILED DESCRIPTION OF THE INVENTION

Definitions

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing, e.g. activity, by a measurable amount. Compounds that modulate CFTR activity, by increasing the activity of the CFTR anion channel, are called agonists. Compounds that modulate CFTR activity, by decreasing the activity of the CFTR anion channel, are called antagonists.

The phrase "treating or reducing the severity of an CFTR mediated disease" refers both to treatments for diseases that are directly caused by CFTR activities and alleviation of symptoms of diseases not directly caused by CFTR anion channel activities. Examples of diseases whose symptoms may be affected by CFTR activity include, but are not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B.

and March, J., John Wiley & Sons, New York: 2001, the entire contents of which are hereby incorporated by reference.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein the term "aliphatic' encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino], amino [e.g., aliphaticamino, cycloaliphaticamino, or heterocycloaliphaticamino], sulfonyl [e.g., aliphaticsulfonyl], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, hydroxyalkyl, aralkyl, (alkoxyaryl)alkyl, (sulfonylamino)alkyl (such as (alkylsulfonylamino)alkyl), aminoalkyl, amidoalkyl, (cycloaliphatic)alkyl, cyanoalkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic, heterocycloaliphatic, aryl, heteroaryl, alkoxy, aroyl, heteroaroyl, acyl [e.g., (cycloaliphatic)carbonyl, or (heterocycloaliphatic)carbonyl], nitro, cyano, acyl [e.g., aliphaticcarbonyl, cycloaliphaticcarbonyl, arylcarbonyl, heterocycloaliphaticcarbonyl or heteroarylcarbonyl], amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, or aliphaticsulfonylamino], sulfonyl [e.g., alkylsulfonyl, cycloaliphaticsulfonyl, or arylsulfonyl], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphaticsulfonyl, aliphaticaminosulfonyl, or cycloaliphaticsulfonyl], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino" These terms when used alone or in connection with another group refers to an amido group such as $N(R^XR^Y)$—C(O)— or $R^YC(O)$—$N(R^X)$— when used terminally and —C(O)—$N(R^X)$— or —$N(R^X)$—C(O)— when used internally, wherein $R^X$ and $R^Y$ are defined below. Examples of amido groups include alkylamido (such as alkylcarbonylamino or alkylcarbonylamino), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic) carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic ring systems include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl or cycloaliphaticsulfinyl]; sulfanyl [e.g., aliphaticsulfanyl]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkylsulfonyl and arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicyclic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiophenyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety such as tetrahydroisoquinoline. A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (aralipathic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (aralipathic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pyranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (aralipathic)oxy; (heteroaralipathic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (aralipathic)carbonyl; (heterocycloaliphatic)carbonyl; ((heterocycloaliphatic)aliphatic)carbonyl; or (heteroaralipathic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; [((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaralipathic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ can be aliphatic, aryl, aralipathic, heterocycloaliphatic, heteroaryl, or heteroaralipathic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1, 2, or 3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include alkylsulfanyl.

As used herein a "sulfinyl" group refers to —S(O)—R$^X$ when used terminally and —S(O)— when used internally, wherein R$^X$ has been defined above.

As used herein, a "sulfonyl" group refers to —S(O)$_2$—R$^X$ when used terminally and —S(O)$_2$— when used internally, wherein R$^X$ has been defined above.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure (R$^X$R$^Y$)N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidino" group refers to the structure —N=C(N(R$^X$R$^Y$))N(R$^X$R$^Y$) wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, the term "amidino" group refers to the structure —C=(NR$^X$)N(R$^X$R$^Y$) wherein R$^X$ and R$^Y$ have been defined above.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$- where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, $R_3$, and $R_4$, and other variables contained therein formulae I encompass specific groups, such as alkyl and aryl. Unless otherwise noted, each of the specific groups for the variables $R_1$, $R_2$, $R_3$, and $R_4$, and other variables contained therein can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Compounds

Compounds of the present invention are useful modulators of CFTR and are useful in the treatment of CFTR mediated diseases.

Generic Compounds

The present invention includes a compound of formula (I),

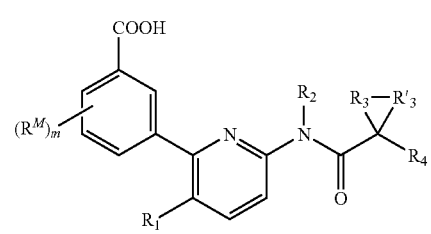

(I)

or a pharmaceutically acceptable salt thereof, wherein:

m is 0-4;

Each $R_M$ is independently $-Z^M R_{11}$, wherein each $Z^M$ is independently a bond or an optionally substituted branched or straight $C_{1-6}$ aliphatic chain wherein up to two carbon units of $Z^M$ are optionally and independently replaced by $-CO-$, $-CS-$, $-CONR^N-$, $-CO_2-$, $-COO-$, $-NR^N CO_2-$, $-O-$, $-OCONR^N-$, $-NR^N CO-$, $-S-$, $-SO-$, $-SO_2-$, or $-NR^N-$.

Each $R_{11}$ is independently $R^N$, halo, $-OH$, $-NH_2$, $-NO_2$, $-CN$, $-CF_3$, or $-OCF_3$.

Each $R^N$ is independently hydrogen or an optionally substituted $C_{1-8}$ aliphatic group.

Each $R_1$ is a $C_{1-6}$ aliphatic;

Each $R_2$ is hydrogen or an optionally substituted $C_{1-6}$ aliphatic;

Each $R_3$ and $R'_3$ together with the carbon atom to which they are attached form an unsubstituted $C_{3-7}$ cycloalkyl ring;

Each $R_4$ is:

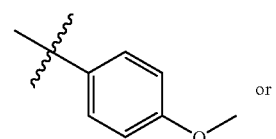

(i)

or

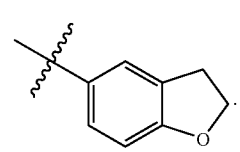

(ii)

Specific Embodiments

Substituent $R_1$

In some embodiments, $R_1$ is an optionally substituted $C_{1-4}$ aliphatic. In several examples, $R_1$ is an optionally substituted $C_{1-4}$ alkyl, an optionally substituted $C_{2-4}$ alkenyl, or an optionally substituted $C_{2-4}$ alkynyl. In several examples, $R_1$ is $C_{1-3}$ alkyl. Exemplary $R_1$ include methyl, ethyl, or isopropyl.

Substituent $R_2$

Each $R_2$ can be hydrogen. Or, each $R_2$ can be a $C_{1-6}$ aliphatic.

In several embodiments, $R_2$ is a $C_{1-6}$ aliphatic optionally substituted with 1, 2, or 3 halo, $C_{1-2}$ aliphatic, or alkoxy. In several examples, $R_2$ can be substituted methyl, ethyl, propyl, or butyl. In several examples, $R_2$ can be methyl, ethyl, propyl, or butyl.

In several embodiments, $R_2$ is hydrogen.

Substituents $R_3$ and $R'_3$

Each $R_3$ and $R'_3$ together with the carbon atom to which they are attached form a $C_{3-6}$ cycloalkyl ring. In several embodiments, $R_3$ and $R'_3$ together with the carbon atom to which they are attached form a cyclopropyl or cyclopentyl ring. In one embodiment, $R_3$ and $R'_3$ together with the carbon atom to which they are attached form a cyclopropyl ring.

Substituent $R_4$

In several embodiments, $R_4$ is:

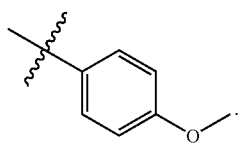

(i)

In several embodiments, $R_4$ is:

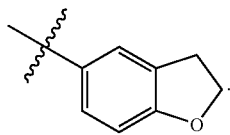

(ii)

Exemplary Compound Families

In another aspect, the present invention includes compounds of formula II:

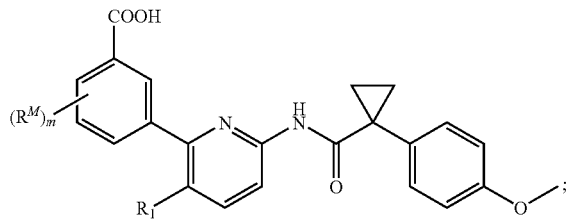

II or a pharmaceutically acceptable salt thereof,
wherein:
$R_1$ is C1-C4 alkyl;
$R^M$ and m are as defined above.

In some embodiments of formula II, m is 0.

In some embodiments, $R_1$ is selected from the group consisting of methyl, ethyl, i-propyl, or t-butyl.

In some embodiments of formula II, m is 0 and $R_1$ is methyl.

In another aspect, the present invention includes compounds of formula III:

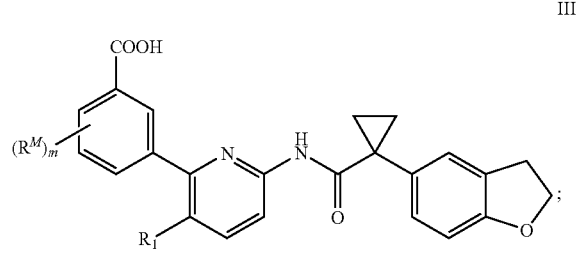

III or a pharmaceutically acceptable salt thereof,
wherein:
$R_1$ is C1-C4 alkyl;
$R^M$ and m are as defined above.

In some embodiments of formula II, m is 0.

In some embodiments, $R_1$ is selected from the group consisting of methyl, ethyl, i-propyl, or t-butyl.

In some embodiments of formula II, m is 0 and $R_1$ is methyl.

Exemplary compounds of the present invention include, but are not limited to, those illustrated in Table 1 below.

TABLE 1

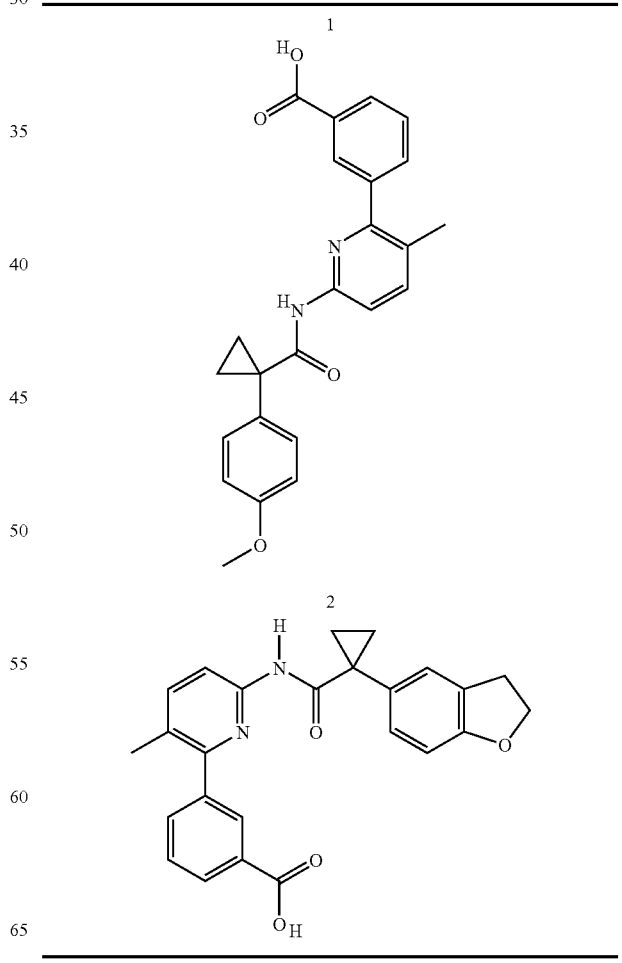

Synthetic Schemes
Compounds of the invention may be prepared by known methods or as illustrated in the schemes below.

Scheme 1
Preparation of phenylacetonitriles

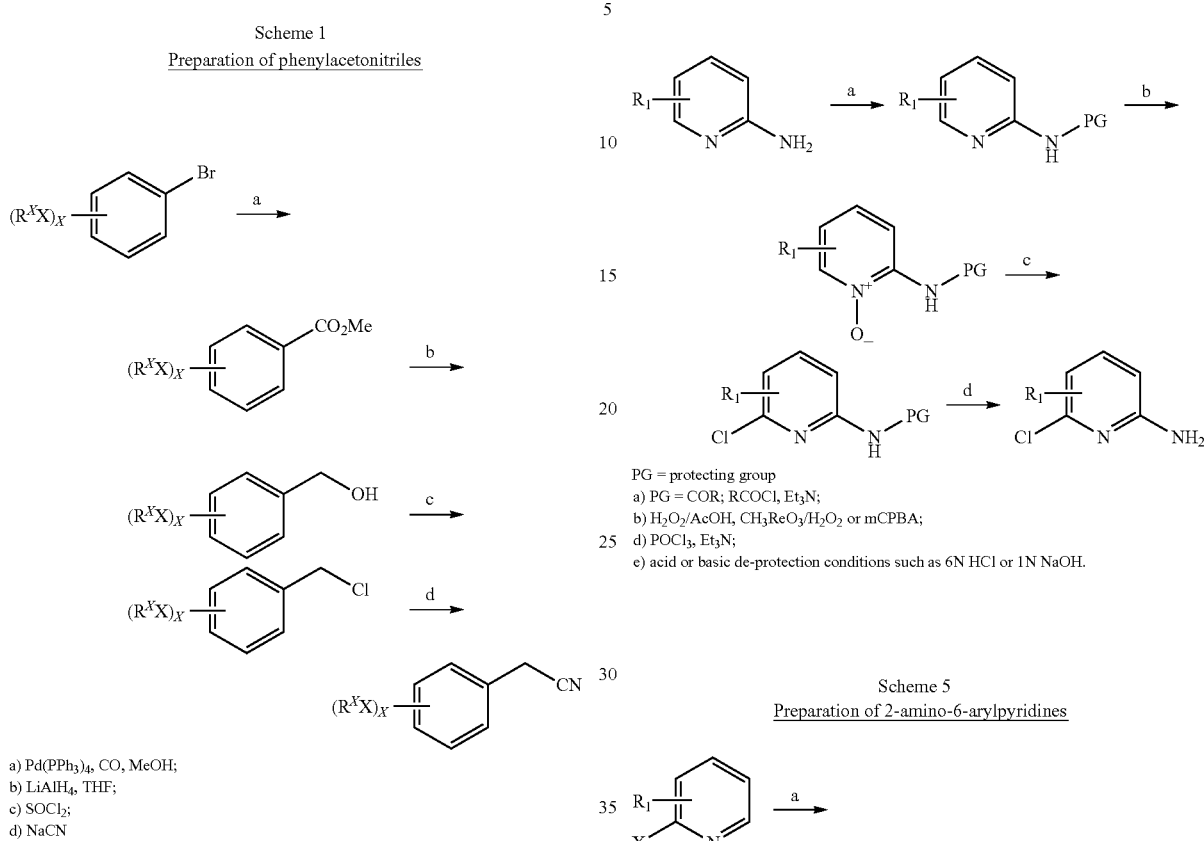

a) Pd(PPh$_3$)$_4$, CO, MeOH;
b) LiAlH$_4$, THF;
c) SOCl$_2$;
d) NaCN

Scheme 2
Preparation of cyclopropylcarboxylic acids

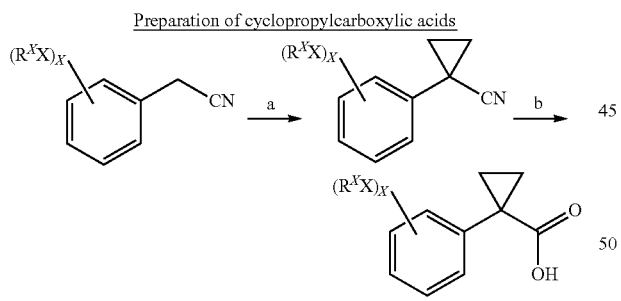

a) ClCH$_2$CH$_2$Br, NaOH, BTEAC;
b) NaOH, Δ

Scheme 3
Preparation of acid chlorides

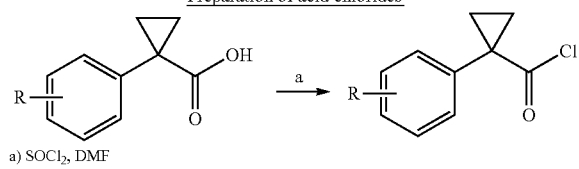

a) SOCl$_2$, DMF

Scheme 4
Preparation of 2-amino-6-chloropyridines

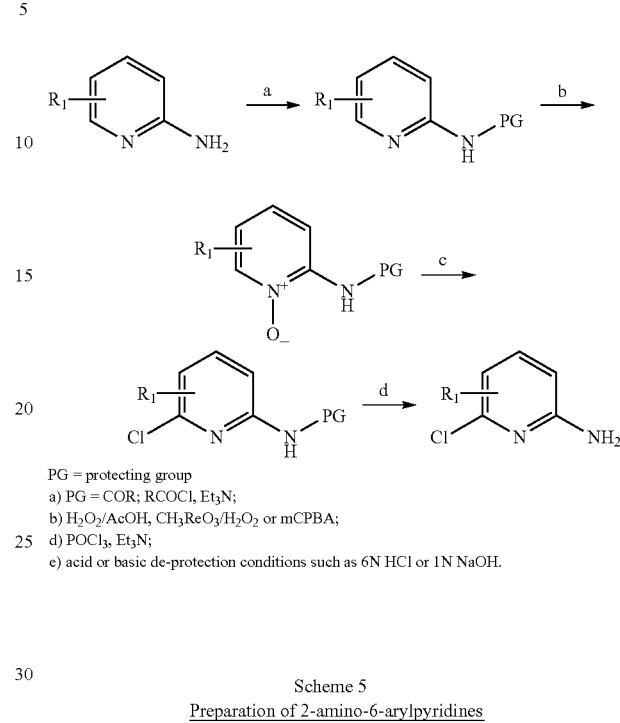

PG = protecting group
a) PG = COR; RCOCl, Et$_3$N;
b) H$_2$O$_2$/AcOH, CH$_3$ReO$_3$/H$_2$O$_2$ or mCPBA;
d) POCl$_3$, Et$_3$N;
e) acid or basic de-protection conditions such as 6N HCl or 1N NaOH.

Scheme 5
Preparation of 2-amino-6-arylpyridines

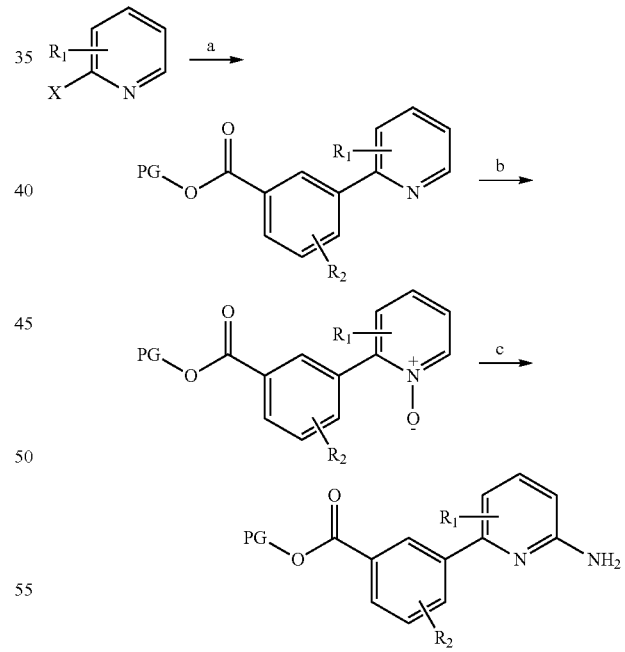

X = Cl, Br, I; PG = protecting group like methyl or tBu; M = SnR$_3$, B(OR$_3$)$_2$, or ZnCl.

a) 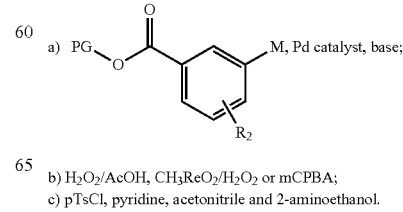 M, Pd catalyst, base;

b) H$_2$O$_2$/AcOH, CH$_3$ReO$_2$/H$_2$O$_2$ or mCPBA;
c) pTsCl, pyridine, acetonitrile and 2-aminoethanol.

Scheme 6
Preparation of arylboronic acids

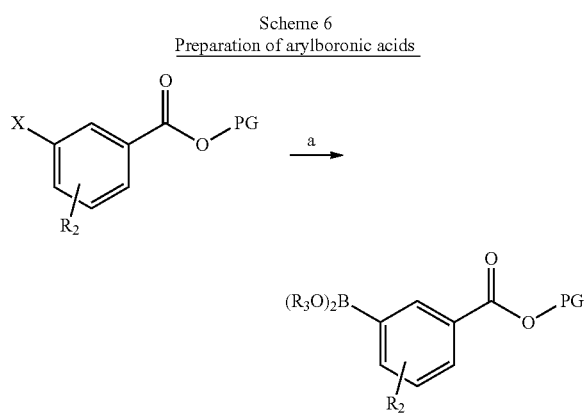

X = Cl, Br, I and PG = protecting group like methyl or tBu;
a) (R₃O)₂B—B(OR₃)₂, Pd(dppf)Cl₂, KOAc, DMF or DMSO

Scheme 7
Preparation of final compounds
Method 1:

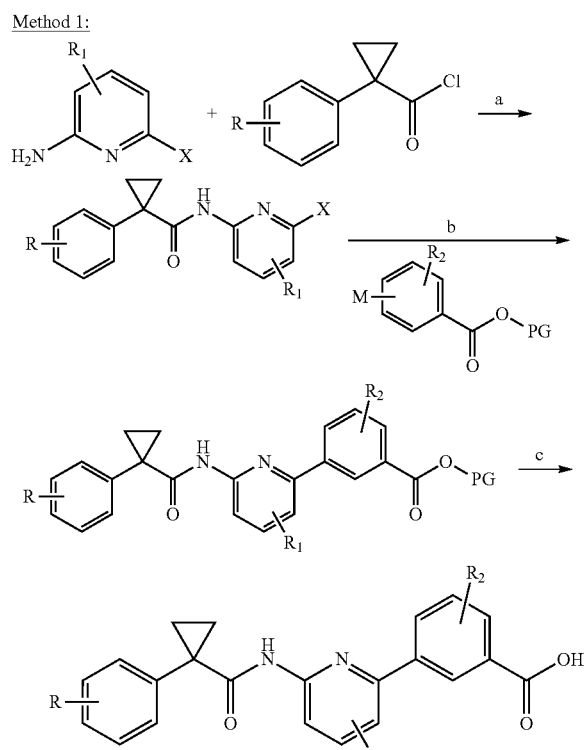

Examples of M are —SnR₃, B(OH)₂, B(OR₃)₂, ZnCl, MgCl; X = Cl, Br, I
a) Et₃N, CH₂Cl₂;
b) Pd catalyst, base;
c) de-protection conditions such as TFA in CH₂Cl₂ or LiOH in dioxane.

Method 2:

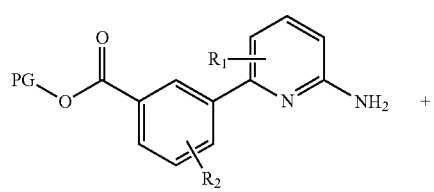

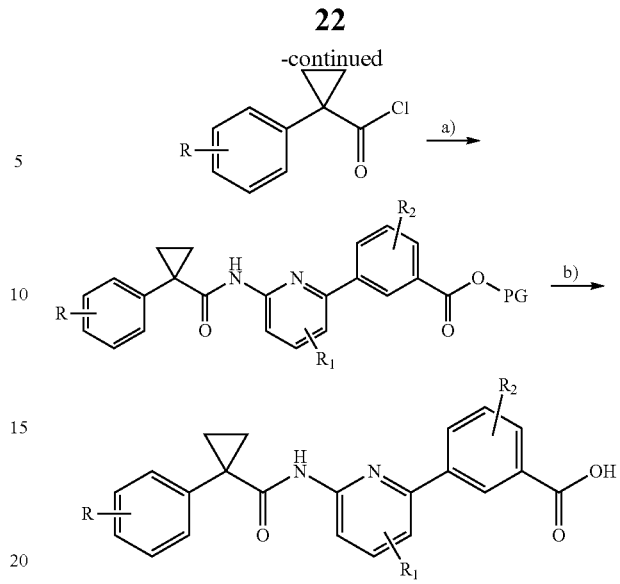

a) Et₃N, CH₂Cl₂;
b) de-protection conditions such as TFA in CH₂Cl₂ or LiOH in dioxane.

Formulations, Administrations, and Uses
Pharmaceutically Acceptable Compositions Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formulae (I) to a subject, preferably a mammal, in need thereof.

In certain preferred embodiments, the present invention provides a method of treating Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker disease, secretory diarrhea, polycystic kidney disease, chronic obstructive pulmonary disease (COPD), dry eye disease, and Sjögren's Syndrome, comprising the step of administering to said mammal an effective amount of a composition comprising a compound of formulae (I) or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formulae (I) or a preferred embodiment thereof as set forth above.

According to the invention an "effective amount" of the compound or pharmaceutically acceptable composition is that amount effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay- Sachs, Crigler-Najjar type II, Polyendocrinopathy/ Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of CFTR. Thus, without wishing to be bound by any particular theory, the compounds and compositions are particularly useful for treating or lessening the severity of a disease, condition, or disorder where hyperactivity or inactivity of CFTR is implicated in the disease, condition, or disorder. When hyperactivity or inactivity of CFTR is implicated in a particular disease, condition, or disorder, the disease, condition, or disorder may also be referred to as an "CFTR-mediated disease, condition or disorder". Accordingly, in another aspect, the present invention provides a method for treating or lessening the severity of a disease, condition, or disorder where hyperactivity or inactivity of an CFTR is implicated in the disease state.

The activity of a compound utilized in this invention as a modulator of CFTR may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR activity in a biological sample is useful for a variety of purposes that are known to one of skill in the art. Examples of such purposes include, but are not limited to, the study of CFTR activity in biological and pathological phenomena and the comparative evaluation of new modulators of CFTR activity.

In yet another embodiment, a method of modulating activity of an anion channel in vitro or in vivo, is provided comprising the step of contacting said channel with a compound of the present invention. In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with a compound of the present invention. The term "functional CFTR" as used herein means an CFTR activity that is capable of transport activity.

According to another preferred embodiment, the activity of the CFTR activity is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a CFTR activity or a fragment thereof in a biological sample in vitro or in vivo comprising (i) a composition comprising a compound of the present invention; and (ii) instructions for a.) contacting the composition with the biological sample and b.) measuring activity of said CFTR activity or a fragment thereof. In one embodiment, the kit further comprises instructions for a.) contacting an additional composition with the biological sample; b.) measuring the activity of said CFTR activity or a fragment thereof in the presence of said additional compound, and c.) comparing the activity of the CFTR activity in the presence of the additional compound with the density of the CFTR activity in the presence of a compound of the present invention.

Preparations and Examples

F. tert-Butyl 3-(6-amino-3-methylpyridin-2-yl)benzoate

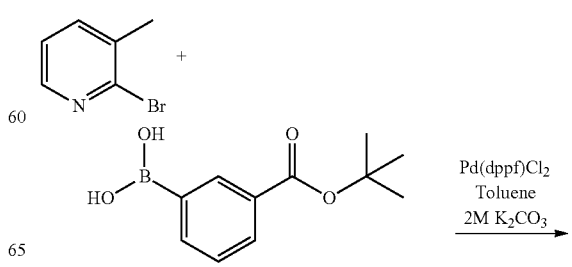

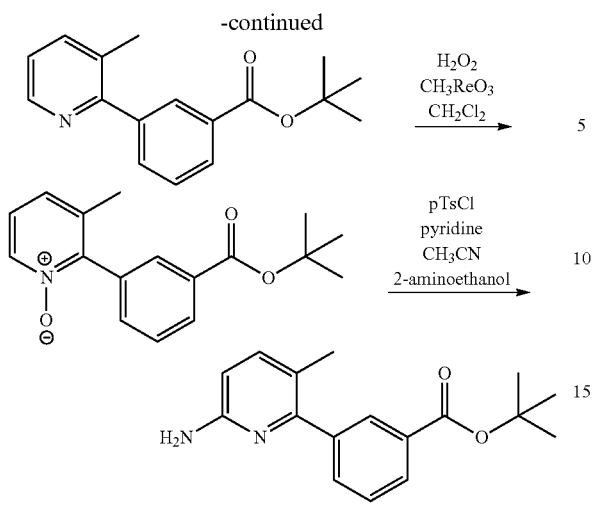

Step a: tert-Butyl 3-(3-methylpyridin-2-yl)benzoate

2-Bromo-3-methylpyridine (50.0 g, 291 mmol), 3-(tert-butoxycarbonyl)phenyl-boronic acid (68.4 g, 308 mmol), potassium carbonate (96.4 g, 697 mmol), and dichloro[1,1'-bis(diphenylphosphino)ferrocene]palladium (II) dichloromethane adduct (Pd(dppf)Cl$_2$, 3.19 g, 3.91 mmol) were dissolved in a mixture of 1.5 L of toluene and 350 mL of water. The resulting solution was stirred and heated at 80° C. for 16 hours. The reaction mixture was cooled to 25° C. and then the layers were separated. The organic layer was evaporated to dryness and was then purified on 3 kg of silica gel utilizing a gradient of 0-18.5% ethylacetate in hexanes to yield tert-butyl 3-(3-methylpyridin-2-yl)benzoate as a pale yellow oil (49.3 g, 63%). ESI-MS m/z calc. 269.1. found 270.2 (M+1)$^+$. Retention time 0.93 minutes Step b: 2-(3-(tert-Butoxycarbonyl)phenyl)-3-methylpyridine 1-oxide tert-Butyl 3-(3-methylpyridin-2-yl)benzoate (49.6 g, 184 mmol) was dissolved in a mixture of 75 mL of dichloromethane and 40 mL of 30% hydrogen peroxide. Methyltrioxorhenium (VII) (2.35 g, 9.44 mmol) was added and the reaction mixture was stirred vigorously for 16 hours. The layers were then separated and the organic layer was treated with sodium sulfite and then dried over sodium sulfate. The crude product was then poured onto a pad of silica gel and washed with ethyl acetate. The product was then eluted from the silica gel pad with a mixture of 10% (v/v) methanol in ethyl acetate to yield 2-(3-(tert-butoxycarbonyl)phenyl)-3-methylpyridine 1-oxide (29.8 g, 57%) as a white solid. ESI-MS m/z calc. 285.1. found 286.1 (M+1)$^+$. Retention time 1.22 minutes.

Step c: tert-Butyl 3-(6-amino-3-methylpyridin-2-yl)benzoate 2-(3-(tert-Butoxycarbonyl)phenyl)-3-methylpyridine 1-oxide (29.8 g, 104 mmol) was dissolved in a mixture of acetonitrile (662 mL) and pyridine (33.8 mL, 418 mmol) under an atmosphere of argon. 4-Methylbenzene-1-sulfonyl chloride (pTsCl, 25.9 g, 136 mmol) was added and the reaction mixture was heated at 75° C. for 5 hours. 2-Aminoethanol (166 mL, 2.75 mol) was added after allowing the reaction mixture to cool to room temperature. After one hour, the acetonitrile was evaporated and the crude product was partitioned between ethyl acetate and a saturated aqueous solution of sodium chloride. The layers were separated and the organic layer was evaporated to dryness and then purified on 1.5 kg of silica gel utilizing a gradient of 0-100% ethyl acetate in hexanes to yield tert-butyl 3-(6-amino-3-methylpyridin-2-yl)benzoate (15.2 g, 51%) as a white solid. ESI-MS m/z calc. 284.1, found 285.2 (M+1)$^+$. Retention time 1.16 minutes. $^1$H NMR (400 MHz, DMSO-d$_6$) δ 7.99-7.98 (m, 1H), 7.90-7.87 (m, 1H) 7.72-7.7.69 (m, 1H), 7.52 (t, J=7.7 Hz, 1H), 7.31 (d, J=8.3 Hz, 1H), 6.42 (d, J=8.3 Hz, 1H), 5.83 (s, 2H), 2.11 (s, 3H), 1.54 (s, 9H).

G. 3-(6-(1-(4-Methoxyphenyl)cyclopropanecarboxamido)-3-methylpyridin-2-yl)benzoic acid

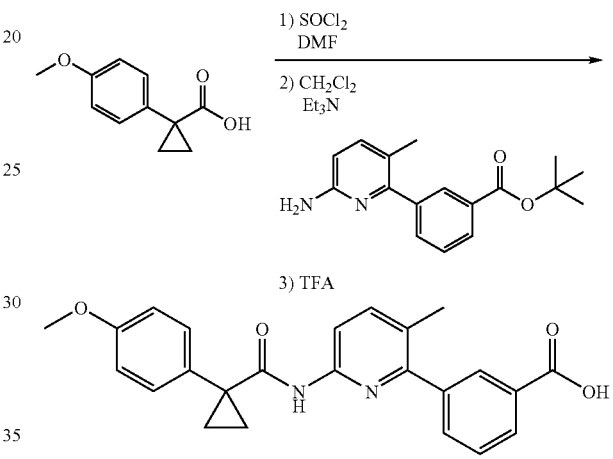

1-(4-Methoxyphenyl)cyclopropanecarboxylic acid (57.7 mg, 0.300 mmol) was placed in an oven-dried flask which was allowed to cool under nitrogen. Thionyl chloride (0.3 mL) and N,N-dimethylformamide (0.03 mL) were added and the solution was allowed to stir for 30 minutes. The excess thionyl chloride was removed under vacuum and the resulting oil was re-dissolved in dichloromethane containing triethylamine (0.125 mL, 0.900 mmol). tert-Butyl 3-(6-amino-3-methylpyridin-2-yl)benzoate (85.3 mg, 0.300 mmol) was added and the reaction mixture was allowed to stir for 3 hours. Trifluoroacetic acid (1 mL) was added and the solution was allowed to stir for an additional 3 hours. The mixture was evaporated to dryness, dissolved in a minimum of N,N-dimethylformamide and then purified by reverse-phase preparative liquid chromatography utilizing a gradient of 0-99% acetonitrile in water containing 0.05% trifluoroacetic acid to yield 3-(6-(1-(4-methoxyphenyl)cyclopropane carboxamido)-3-methylpyridin-2-yl)benzoic acid. ESI-MS m/z calc. 402.2, found; 403.1 (M+1)$^+$ Retention time 1.65 minutes.

H. 1-(2,3-Dihydrobenzofuran-5-yl)cyclopropanecarboxylic acid

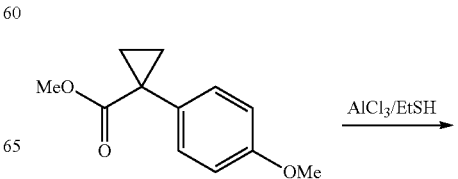

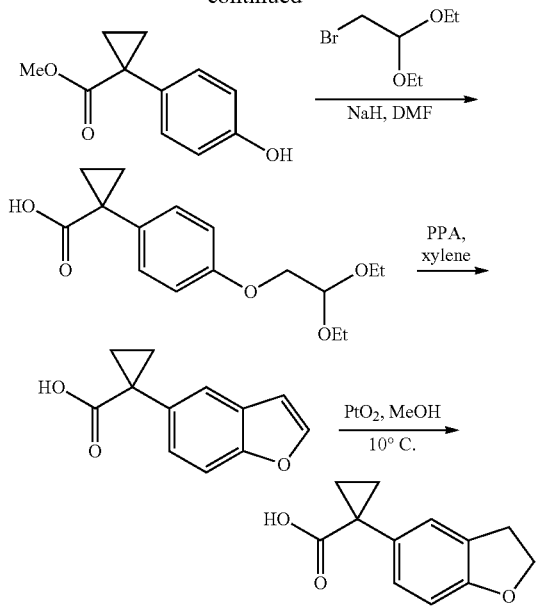

Step a:
1-(4-Hydroxy-phenyl)-cyclopropanecarboxylic acid methyl ester

To a solution of methyl 1-(4-methoxyphenyl)cyclopropanecarboxylate (10.0 g, 48.5 mmol) in dichloromethane (80 mL) was added EtSH (16 mL) under ice-water bath. The mixture was stirred at 0° C. for 20 min before AlCl$_3$ (19.5 g, 0.150 mmol) was added slowly at 0° C. The mixture was stirred at 0° C. for 30 min. The reaction mixture was poured into ice-water, the organic layer was separated, and the aqueous phase was extracted with dichloromethane (50 mL×3). The combined organic layers were washed with H$_2$O, brine, dried over Na$_2$SO$_4$ and evaporated under vacuum to give 1-(4-hydroxy-phenyl)-cyclopropanecarboxylic acid methyl ester (8.9 g, 95%). $^1$H NMR (400 MHz, CDCl$_3$) δ 7.20-7.17 (m, 2H), 6.75-6.72 (m, 2H), 5.56 (s, 1H), 3.63 (s, 3H), 1.60-1.57 (m, 2H), 1.17-1.15 (m, 2H).

Step b: 1-[4-(2,2-Diethoxy-ethoxy)-phenyl]-cyclopropanecarboxylic acid

To a stirred solution of 1-(4-hydroxy-phenyl)-cyclopropanecarboxylic acid methyl ester (15.0 g, 84.3 mmol) in DMF (50 mL) was added sodium hydride (6.7 g, 170 mmol, 60% in mineral oil) at 0° C. After hydrogen evolution ceased, 2-bromo-1,1-diethoxy-ethane (16.5 g, 84.3 mmol) was added drop-wise to the reaction mixture. The reaction was stirred at 160° C. for 15 hours. The reaction mixture was poured onto ice (100 g) and extracted with dichloromethane. The combined organics were dried over Na$_2$SO$_4$. The solvent was evaporated under vacuum to give crude 1-[4-(2,2-diethoxy-ethoxy)-phenyl]-cyclopropanecarboxylic acid (10 g), which was used directly in the next step without purification.

Step c: 1-Benzofuran-5-yl-cyclopropanecarboxylic acid

To a suspension of crude 144-(2,2-diethoxy-ethoxy)-phenyl]-cyclopropanecarboxylic acid (20 g, ~65 mmol) in xylene (100 mL) was added PPA (22.2 g, 64.9 mmol) at room temperature. The mixture was heated at reflux (140° C.) for 1 hour before it was cooled to room temperature and decanted from the PPA. The solvent was evaporated under vacuum to obtain the crude product, which was purified by preparative HPLC to provide 1-(benzofuran-5-yl)cyclopropanecarboxylic acid (1.5 g, 5%). $^1$H NMR (400 MHz, DMSO-d$_6$) δ 12.25 (br s, 1H), 7.95 (d, J=2.8 Hz, 1H), 7.56 (d, J=2.0 Hz, 1H), 7.47 (d, J=11.6 Hz, 1H), 7.25 (dd, J=2.4, 11.2 Hz, 1H), 6.89 (d, J=1.6 Hz, 1H), 1.47-1.44 (m, 2H), 1.17-1.14 (m, 2H).

Step d: 1-(2,3-Dihydrobenzofuran-5-yl)cyclopropanecarboxylic acid

To a solution of 1-(benzofuran-5-yl)cyclopropanecarboxylic acid (700 mg, 3.47 mmol) in MeOH (10 mL) was added PtO$_2$ (140 mg, 20%) at room temperature. The stirred reaction mixture was hydrogenated under hydrogen (1 atm) at 10° C. for 3 days. The reaction mixture was filtered. The solvent was evaporated under vacuum to afford the crude product, which was purified by preparative HPLC to give 1-(2,3-dihydrobenzofuran-5-yl)cyclopropanecarboxylic acid (330 mg, 47%). $^1$H NMR (400 MHz, CDCl$_3$) δ 7.20 (s, 1H), 7.10 (d, J=10.8 Hz, 1H), 6.73 (d, J=11.2 Hz, 1H), 4.57 (t, J=11.6 Hz, 2H), 3.20 (t, J=11.6 Hz, 2H), 1.67-1.63 (m, 2H), 1.25-1.21 (m, 2H).

I. 3-(6-(1-(2,3-Dihydrobenzofuran-5-yl)cyclopropanecarboxamido)-3-methylpyridin-2-yl)benzoic acid

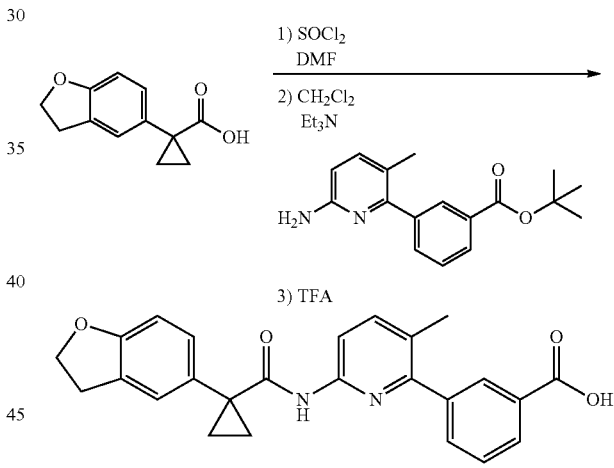

1-(2,3-Dihydrobenzofuran-5-yl)cyclopropanecarboxylic acid (24.0 mg, 0.118 mmol) was placed in an oven-dried flask which was allowed to cool under nitrogen. Thionyl chloride (0.3 mL) and N,N-dimethylformamide (0.03 mL) were added and the solution was allowed to stir for 30 minutes. The excess thionyl chloride was removed under vacuum and the resulting oil was re-dissolved in dichloromethane containing triethylamine (0.0495 mL, 0.353 mmol). tert-Butyl 3-(6-amino-3-methylpyridin-2-yl)benzoate (33.4 mg, 0.118 mmol) was added and the reaction mixture was allowed to stir for 3 hours. Trifluoroacetic acid (1 mL) was added and the solution was allowed to stir for an additional 3 hours. The mixture was evaporated to dryness, dissolved in a minimum of N,N-dimethylformamide and then purified by reverse-phase preparative liquid chromatography utilizing a gradient of 0-99% acetonitrile in water containing 0.05% trifluoroacetic acid to yield 3-(6-(1-(2,3-dihydrobenzofuran-5-yl)cyclo-propanecarboxamido)-3-methylpyridin-2-yl)benzoic acid. ESI-MS m/z calc. 414.2, found; 415.0 (M+1)$^+$ Retention time 1.64 minutes.

Assays
Assays for Detecting and Measuring ΔF508-CFTR Correction Properties of Compounds Membrane potential optical methods for assaying ΔF508-CFTR modulation properties of compounds The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with F508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes. Solutions Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

DiSBAC$_2$(3): Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours Electrophysiological Assays for assaying ΔF508-CFTR modulation properties of compounds 2. Using Chamber Assay Using chamber experiments were performed on polarized epithelial cells expressing ΔF508-CFTR to further characterize the ΔF508-CFTR modulators identified in the optical assays. FRT$^{\Delta F508-CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm$^2$ or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

3. Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), CaCl$_2$ (1.2), MgCl$_2$ (1.2), K$_2$HPO$_4$ (2.4), KHPO$_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR (FRT$^{\Delta F508\text{-}CFTR}$) were used for Ussing chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl$^-$ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 μl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 μM forskolin and 20 μM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 UV of the test compound for 24 hours at 37° C. and the current density was compared to the 27° C. and 37° C. controls (% activity). Prior to recording, the cells were washed 3× with extracellular recording medium to remove any remaining test compound. Preincubation with 10 μM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl$^-$ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), $MgCl_2$ (1), HEPES (10), and 240 μg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the non-specific phosphatase inhibitor F$^-$ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing 2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

12. Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), $MgCl_2$ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

The exemplified compounds of Table 1 have an activity as shown below in Table 3.

TABLE 3

| Cmpd # | EC50 | Efficacy |
|---|---|---|
| 1 | +++ | +++ |
| 2 | +++ | +++ |

Table 3
IEC50: +++ <= 2.0 μM < ++ <= 5.0 μM < +
Percent Efficacy: + <= 25.0% < ++ <= 100.0% < +++

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of treating or lessening the severity of a disease in a patient, wherein said disease is dry-eye disease, said method comprising the step of administering to said patient an effective amount of a compound according to formula I:

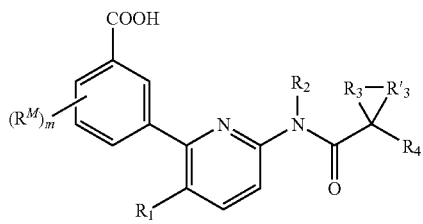

or a pharmaceutically acceptable salt thereof, wherein independently for each occurrence:

m is 0-4;

$R_M$ is $-Z^M R_{11}$, wherein each $Z^M$ is a bond or an optionally substituted branched or straight $C_{1-6}$ aliphatic chain wherein up to two carbon units of $Z^M$ are optionally replaced by —CO—, —CS—, —CONR$^N$—, —CO$_2$—, —OCO—, —NR$^N$CO$_2$—, —O—, —OCONR$^N$—, —NR$^N$CO—, —S—, —SO—, —SO$_2$—, or —NR$^N$—;

$R_{11}$ is $R^N$, halo, —OH, —NH$_2$, —NO$_2$, —CN, —CF$_3$, or —OCF$_3$;

$R^N$ is H or an optionally substituted C1-C8 aliphatic;

$R_1$ is a C1-C6 aliphatic;

$R_2$ is H or an optionally substituted C1-C6 aliphatic;

$R_3$ and $R'_3$ together with the carbon atom to which they are attached form an unsubstituted $C_{3-7}$ cycloalkyl ring; and $R_4$ is:

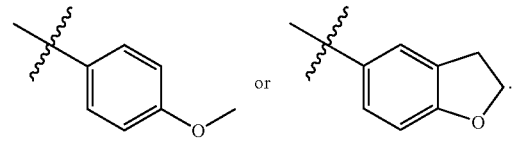

2. The method of claim 1, wherein $R_1$ is an optionally substituted C1-C4 aliphatic.

3. The method of claim 1, wherein $R_1$ is an optionally substituted C1-C4 alkyl.

4. The method of claim 1, wherein $R_1$ is methyl, ethyl, propyl, or butyl.

5. The method of claim 1, wherein $R_2$ is H.

6. The method of claim 1, wherein $R_2$ is a C1-C6 aliphatic.

7. The method of claim 1, wherein $R_2$ is a C1-C6 alkyl.

8. The method of claim 1, wherein $R_2$ is methyl, ethyl, propyl, butyl, pentyl, or hexyl.

9. The method of claim 1, wherein $R_3$ and $R'_3$ taken together form a cyclopropyl ring.

10. The method of claim 1, wherein $R_3$ and $R'_3$ taken together form a cyclopentyl ring.

11. The method of claim 1, wherein $R_4$ is

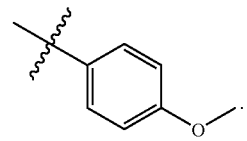

12. The method of claim 1, wherein $R_4$ is

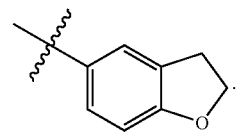

13. The method of claim 1, wherein m is 0.

14. The method of claim 1, wherein the compound is according to formula II:

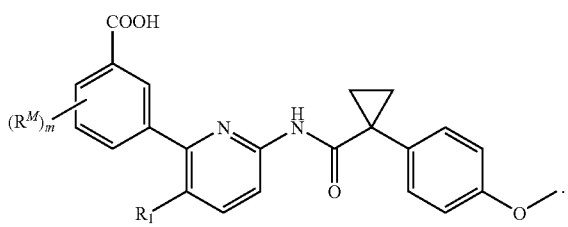

15. The method of claim 14, wherein $R_1$ is methyl.

16. The method of claim 14, wherein m is 0.

17. The method of claim 1, wherein the compound is according to formula III:
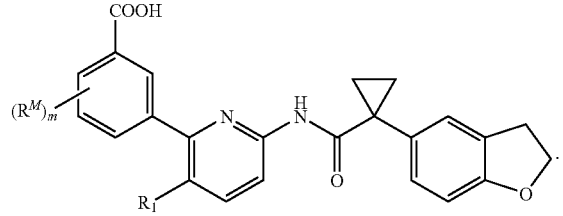
18. The method of claim 17, wherein R₁ is methyl.
19. The method of claim 17, wherein m is 0.
20. The method of claim 1, wherein the compound is
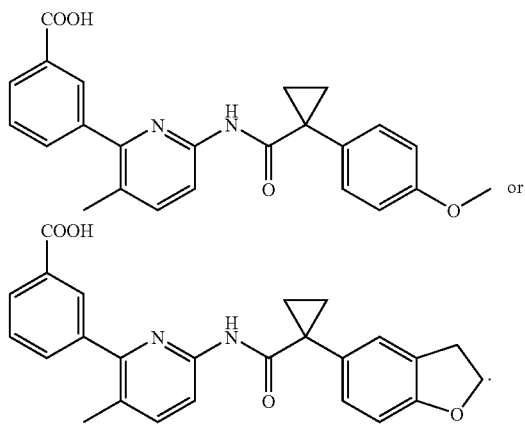
* * * * *